(12) United States Patent
Sabatier et al.

(10) Patent No.: US 7,894,305 B2
(45) Date of Patent: Feb. 22, 2011

(54) METHODS FOR DETECTING HUMANS

(75) Inventors: James M. Sabatier, Oxford, MS (US);
Alexander E. Ekimov, Oxford, MS (US); Carl K. Frederickson, Conway, AR (US)

(73) Assignee: University of Mississippi, University, MS (US)

( * ) Notice: Subject to any disclaimer, the term of this patent is extended or adjusted under 35 U.S.C. 154(b) by 283 days.

(21) Appl. No.: 12/259,076

(22) Filed: Oct. 27, 2008

(65) Prior Publication Data
US 2010/0027378 A1 Feb. 4, 2010

(51) Int. Cl.
*G08B 29/02* (2006.01)
(52) U.S. Cl. ..................................... 367/136
(58) Field of Classification Search .............. 367/136, 367/90, 94
See application file for complete search history.

(56) References Cited

U.S. PATENT DOCUMENTS

| | | | |
|---|---|---|---|
| 5,867,257 A | 2/1999 | Rice et al. | |
| 2006/0195050 A1 | 8/2006 | Alwan et al. | |
| 2006/0288785 A1 | 12/2006 | Zhang et al. | |
| 2010/0027378 A1* | 2/2010 | Sabatier et al. | 367/136 |

FOREIGN PATENT DOCUMENTS

WO    WO 2008063700 A2 *  5/2008

OTHER PUBLICATIONS

Abbott, R.B., "Response Measurement and Harmonic Analysis of Violin Tones," J. Acoust. Soc. Am. 7, 111-116 (1935).
Akay, A. "Acoustics of Friction," J. Acoust. Soc. Am. 111(4), 1525-1548 (2002).
Bass, H. E. and L.N Bolen, "Ultrasonic background noise in industrial environments," J. Acoust. Soc. Am. 78 (6), 2013-2016 (1985).
Biomechanics Force Platform, AMT Inc., Watertown, MA (2005).
Cory, P., H. R. Everett, and T. H. Pastore, "Radar-based intruder detection for a robotic security system," SPIE Proc. 3525: Mobile Robots XIII and Intelligent Transportation Systems, Boston, pp. 62-72 (1998).
Cress, D. H., "Terrain considerations and data base development for the design and testing of devices to detect intruder-induced ground motion," Vicksburg, Miss.: U.S. Waterways, May 1978.
Ebrahimpour, A. Hamam, R.L. Sack, W.N. Patten, "Measuring and Modeling Dynamic Loads Imposed by Moving Crowds," Journal of Structural Engineering, Dec. 1996, pp. 1468-1474.
Ekimov, A. and J. Sabatier, "Detection and analysis of broadband acoustic signatures from walking humans in quiet and noisy environments," Aug. 2008.
Ekimov, A. and J. Sabatier, "Evaluation of the range of human footstep detection," Aug. 2007.

(Continued)

*Primary Examiner*—Dan Pihulic
(74) *Attorney, Agent, or Firm*—Stites & Harbison PLLC; Richard S. Myers, Jr.

(57) ABSTRACT

A method of detecting a human, that includes (a) measuring the ultrasonic signal emitted from human footsteps; (b) measuring the human body motion Doppler signature; reviewing the measurements of steps (a) and (b); and (d) determining the presence of a human.

28 Claims, 7 Drawing Sheets

OTHER PUBLICATIONS

Ekimov, A. and J. Sabatier, "Human detection range by active Doppler and passive ultrasonic methods," Proc. Of SPIE vol. 6943, 6943OR, (2008).

Ekimov, A. and J. Sabatier, "Human motion analyses using footstep ultrasound and Doppler ultrasound," J. Acoust. Soc. Am. 123 (6), Jun. 2008.

Ekimov, A. and J. Sabatier, "Passive ultrasonic method for human footstep detection."

Ekimov, A. and J. Sabatier, "Ultrasonic wave generation due to human footsteps on the ground," J. Acoust. Soc. Am. 121 (3), Mar. 2007.

Ekimov, and J. M. Sabatier, "Broad frequency acoustic response of ground/floor to human footsteps," Proceedings SPIE, vol. 6241, OL-1-8 (2006).

Ekimov, and J. M. Sabatier, "Vibration and sound signatures of human footsteps in buildings," J. Acoust. Soc. Am., 120 (2), 762-768 (2006).

Ekimov, E. and J. M. Sabatier, "Passive and active ultrasonic methods for human motion detection," Proc. Military Sensing Symposium on Battlefield Acoustics and Magnetic Sensors (2006).

Evans, L.B. and H.E. Bass, "Tables of absorption and velocity of sound in still air at 68°F," Huntsville, Alabama, Wyle Laboratories; Report WR72-2 (1972).

Evans, L.B., H.E. Bass, and L.C. Sutherland, "Atmospheric absorption of sound: theoretical predictions," J. Acoust. Soc. Am. 72, 1565-1575 (1972).

Galbraith, F. W. and M.V. Barton "Ground Loading from Footsteps," Journal of the Acoustical Society of America, 48, 5 (Part2), 1970, pp. 1288-1292.

Geisheimer, J. L., E.F. Greneker, and W.S. Marshall, "A high-resolution Doppler model of human gait," SPIE, Proceedings, vol. 4744, 8-18 (2002).

Houston, K. M. and D. P. McGaffigan, "Spectrum Analysis Techniques for Personnel Detection Using Seismic Sensors," SPIE, Proceedings on Unattended Ground Sensor Technologies and Applications, vol. 5090, 162-173 (2003).

Kleinert, D. E., D. G. Wren, C. Smith, and J. P. Chambers, "Development of an acoustic system to monitor suspended sediments in fluvial systems," Proc. 8th Federal Interagency Sedimentation Conference, Reno, NV Apr. 4, 2006.

Kohle, Monika and Dieter Merkl, "Analyzing Human Gait Patterns for Malfunction Detection", Proceedings of the 2000 ACM symposium on Applied computing, Como, Italy, 2000, vol. 1, pp. 41-45.

Li, X., R.J. Logan, and R.E. Pastore, "Perception of acoustic source characteristics: Walking sounds," J. Acoust. Soc. Am. 90(6), 3036-3049 (1991).

Magori, V., "Ultrasonic sensors in air," IEEE Ultrasonic symposium, Proceedings, pp. 471-481 (1994).

Markov, A.A. "Extension of the limit theorems of probability theory to a sum of variables connected in a chain", reprinted in Appendix B of: R. Howard. Dynamic Probabilistic Systems, vol. 1: Markov Chains. John Wiley and Sons, 1971.

Mouring, S., "Dynamic Response of Floor Systems to Building Occupant Activities," Ph.D. Dissertation, The Johns Hopkins University, 1992.

Otero, M., "Application of a continuous wave radar for human gait recognition," SPIE, Proceedings, vol. 5809, 538-548 (2005).

Sabatier, J., A. Ekimov, "Range limitation for seismic footstep detection," Proc. of SPIE vol. 6963, 69630V-1 (2008).

Sabatier, J., and A. Ekimov, "A review of human signatures in urban environments using seismic and acoustic methods," IEEE International Conference on Technologies for Homeland Security, 2008.

Van Dorp, P., and F.C.A. Groen, "Human walking estimation with radar," IEE Proc. Radar, Sonar and Navigation, V. 150, No. 5, 356-365 (2003).

Walker, C.A. and R. Blair "Leg stiffness and damping factors as a function of running speed," Sport Engineering, 5, 129-139 (2002).

Watters, B.G. "Impact-Noise Characteristics of Female Hard-Heeled Foot Traffic," J. Acoust. Soc. Am. 37(4), 619-630 (1965).

Zhang, Zhaonian, Philippe O. Pouliquen, Allen Waxman, and Andreas G. Andreou, "Acoustic micro-Doppler radar for human gait imaging," J. Acoust. Soc. Am. Express Letters, 121 (3), DOI: 10.1121/1.2437842 (2007).

* cited by examiner

METHODS FOR DETECTING HUMANS

GOVERNMENT SUPPORT

This invention was made with support from the Department of the Army, Army Research Office, under contract W911NF-04-1-0190. The United States government has rights to this invention.

PRIORITY INFORMATION

This application claims priority to International Application no. PCT/US2007/067432, which claims priority to U.S. Patent Application No. 60/794,682, filed Apr. 25, 2006, and U.S. Patent Application No. 60/890,917, filed Feb. 21, 2007, the content of both applications being incorporated herein by reference in their entirety.

FIELD OF THE INVENTION

The present invention relates to the field of human detection. More specifically, an embodiment of the present invention includes methods and equipment for the detection of humans that include measurement of the ultrasonic sound signals emitted from human footsteps and a measurement of the human body motion Doppler signature. Embodiments of the present invention can be used in a variety of fields related to security systems.

BACKGROUND OF THE INVENTION

There are numerous situations where it is important to detect the presence of a human. Examples include within a house, on or near a battlefield, at a border, etc.

There have been prior attempts to accurately and efficiently detect the presence of a human both in enclosures and outdoors. For example, microphones and ground vibration sensors have been used to listen to the sound and vibrations caused by human footsteps. Ground vibration sensors are limited by at least two key phenomena.

The first limitation is the site transfer function. Vibrations produced by forces on the surface of the ground propagate from the source to the receiver in a manner that is controlled by the acoustical soil properties of the ground, the site transfer function. The received signal is the product of the source signal and the site transfer function. For ranges of interest, this transfer function filters the source signal so strongly that it only barely resembles the source signal.

The second important limitation is the vibration coupling of sounds in the air into the ground at the receiver location that either mimic signals that arrive thru the soil or dramatically raise the vibration background level at the sensor.

One example of trying to overcome these disadvantages is the development of sensor packages that combine both microphones and seismic vibration sensors to discriminate between airborne and ground-borne sounds.

Since the physics of the site transfer function precludes a frequency-based detection approach using seismic vibration sensors, various groups have for many years relied on the impulsive nature of human footsteps. See, for example, K. M. Houston and D. P. McGaffigan, "Spectrum Analysis Techniques for Personnel Detection Using Seismic Sensors," SPIE, Proceedings on Unattended Ground Sensor Technologies and Applications, Vol. 5090, 162-173 (2003). While this impulsive processing does aid in detection, these transducers respond to impulsive sounds in the air that couple into the ground as impulses at the sensor. In this case, the more local site transfer function or the phenomena of acoustic-to-seismic coupling at the transducer resembles the above-mentioned site transfer function and results in similar effects. In effect, impulsive sounds in the air are false alarms to this approach. Even if the transducers were in ideal quiet acoustic environments, humans can walk in a stealthy manner that may limit detection ranges to only a very few meters, at best.

Additionally, microphones are plagued by wind noise, even at low wind speeds. Wind or air currents flowing over the surface of the microphone produce pressure fluctuations that severely limit the microphone's dynamic range or its sensitivity to low-level sounds. While windscreens reduce wind noise, these devices bring their own set of undesirable attributes. Most importantly, windscreens need to be physically quite large to work effectively, are difficult to conceal, and are not designed for long term unattended use in harsh weather environments.

An important microphone wind noise phenomenon is that this noise falls off as the inverse of the frequency. Microphones designed to function in the ultrasonic frequency range will not suffer from this dynamic range limitation, but the source signal that one is trying to detect must be in the high frequency range. Microphones designed with high sensitivity to work in the audio frequency band will always result in signals dominated by wind noise.

Clearly, humans have the potential to detect sounds or the presence of footsteps during windy times. Human ears along with their brain "processor" can detect footsteps and easily distinguish between the footsteps of humans, horses, or dogs, for example. The well-known low-frequency roll-off of the human ear's frequency response or "A-weighting" accounts for the ability to detect during windy times. Human ears reduce the effects of the dynamic range limiting process of wind by not being sensitive to low frequencies. Our ability to detect and discriminate between the footstep sounds produced by humans and animals and even between people results from the impulsive nature and the timing of the sounds produced by the foot's interaction with the ground or the gait of the individual or animal and the signal's' frequency content.

SUMMARY OF THE INVENTION

As stated above, an embodiment of the present invention includes methods and equipment for the detection of humans that include measurement of ultrasonic signals emitted from human footsteps and a measurement of the human body motion Doppler signature.

One aspect of the present invention is a method of detecting a human, comprising measuring the ultrasonic signals emitted from (a) human footsteps; (b) ultrasonically measuring the human body motion Doppler signature; (c) reviewing the measurements of steps (a) and (b); and (d) determining the presence of a human. The determination step can indicate the presence of a person in an enclosure, such as a building, or outside. In embodiments of the present invention, steps (a) and (b) are performed simultaneously. The determination step (d) may indicate the presence of a human in an enclosure or an outdoor area.

In embodiments of the present invention, step (a) comprises the utilization of microphone sensors for human footstep detection. Furthermore, the microphone sensors may comprise ultrasonic microphone sensors. In other embodiments of the present invention, the ultrasonic microphones measure frequencies in a narrow band frequency range. An example of a narrow band is the measurement of frequencies in the range of about 24-26 kHz. The ultrasonic microphones measure at least one of the toe slap or weight transfer portions of the human footstep signature.

In other embodiments of the invention, the review step (c) includes the measurement of the sound pressure signature from human footstep signals and/or the review step (c) comprises a Fourier spectrum mathematical operation of the sound pressure signal. In aspects of the invention, the Fourier spectrum is considered as a function of time and a time/frequency analysis is conducted.

In other embodiments of the invention, the measure step (b) comprises transmitting waves to a human body, and receiving the reflected or back-scattered waves. The reflected waves may be frequency-modulated by time-varying motions of human body parts. Furthermore, in other embodiments of the present invention, the measurement step (b) comprises a transmitter to emit a carrier signal and a receiver to recognize a human motion-modulated carrier signal.

In embodiments of the present invention, the transmitting waves are chosen from sound and electromagnetic, radar, ultrasound, laser, IR, or terahertz waves. Preferred are ultrasonic waves. In other embodiments, the Doppler signature is measured by transmitting and receiving ultrasonic waves of a resonance frequency of about 20 kHz to about 10 MHz. In another embodiment, the frequency of transmitting ultrasonic waves is about 40 kHz.

In other aspects of the present invention, the human motion-modulated carrier signal comprises a recognition of a frequency shift of human body motion when the arms and legs move characteristically in relation to the torso.

In yet other embodiments of the present invention, step (a) can comprise measuring the timing between the footstep signal, and step (b) can comprise measuring Doppler shifts associated with appendage motion, and step (c) can comprise a comparison of the two to determine the presence of a human. Additionally, steps (c) and (d) can comprise utilization of the time-frequency analysis to review data obtained in steps (a) and (b) and compare that data to a standard value. In embodiments of the invention, the Markov chain method is used for time-frequency analysis.

The present invention also can be applied to walking or running vertebrate animals.

Additionally, other aspects of the present invention include devices for detecting the presence of a human that comprises an ultrasonic microphone, a Doppler sensor, a data acquisition board, and a control unit.

BRIEF DESCRIPTION OF THE DRAWINGS

FIGS. 5(a) and (b) are the spectrograms of sound pressure at a distance of 5-7 meters from a walker and acceleration at a distance of 1 meter from a walker, respectively. (c) is the time domain signal of acceleration of ten regular, soft, and stealthy footsteps.

DESCRIPTION OF THE INVENTION

Walking people generate unique footstep acoustic and Doppler signatures that can be used for human detection and recognition and to differentiate them from other moving objects. Human footstep acoustic signatures have a broadband frequency response from a few Hertz up to ultrasonic frequencies and generate both vibration in the floor and sound in the air by an interaction of the foot and the supporting surface. Human Doppler signatures result from the oscillation of the human body legs, arms, torso, and head as a result of human movement.

As a result of the biomechanical nature of a footstep, there are two characteristic frequency bands in the vibration and sound responses of footstep signatures. The first or low-frequency band is generated by the component of the footstep force normal to the supporting surface and is concentrated in a low-frequency range below 200 Hz. This frequency band has been typically used for seismic human footstep detectors. The second human footstep frequency band is generated by the tangential friction force of the footstep and is located in a high-frequency range, above 1 kHz up to ultrasonic frequencies. Different walking styles (regular, soft and stealthy) result in different vibration signatures in the low-frequency range that determine the maximum ranges for this method of footstep detection. For example, the stealthy walking style is undetectable even a few meters from a seismic detector.

Radar Doppler signatures of the motion of human legs, arms, torso and head for walking people have been investigated and the results have been presented in a number of publications. See, for example, J. L. Geisheimer, E. F. Greneker, and W. S. Marshall, "A high-resolution Doppler model of human gait," SPIE, Proceedings, Vol. 4744, 8-18 (2002); P. van Dorp, and F. C. A. Groen, "Human walking estimation with radar," IEE Proc. Radar, Sonar and Navigation, V. 150, No. 5, 356-365 (2003); M. Otero, "Application of a continuous wave radar for human gait recognition," SPIE, Proceedings, Vol. 5809, 538-548 (2005); P. Cory, H. R. Everett, and T. H. Pastore, "Radar-based intruder detection for a robotic security system," SPIE Proc. 3525: Mobile Robots XIII and Intelligent Transportation Systems, Boston, pp. 62-72 (1998).

Doppler ultrasound signatures from the motion of the human appendages for walking people were investigated and results are comparable to Doppler radar. Low-cost, low-power ultrasonic motion sensors have been used in a wide range of applications since the 1970s. Benefits of using ultrasonic continuous wave (CW) Doppler sensors include the low-cost, low-electric noise, small size and weight of ceramic transducers and receivers, and the usage of the low-cost, data acquisition boards for signal processing, recording, and analysis.

Embodiments of the present invention incorporate the use of both passive and active ultrasonic methods to exploit unique, human, high-frequency footstep sound pressure and human motion Doppler signatures of body appendages for detection and recognition. Ultrasonic sensors with different frequency bands for passive and active methods can be assembled in small enclosures to function as low-bandwidth, human activity sensors. The simultaneous measurement of the footstep ultrasound and human body Doppler motion effects with sensor-coupled signal processing will provide false alarm-free human detection sensors.

Figure 1:
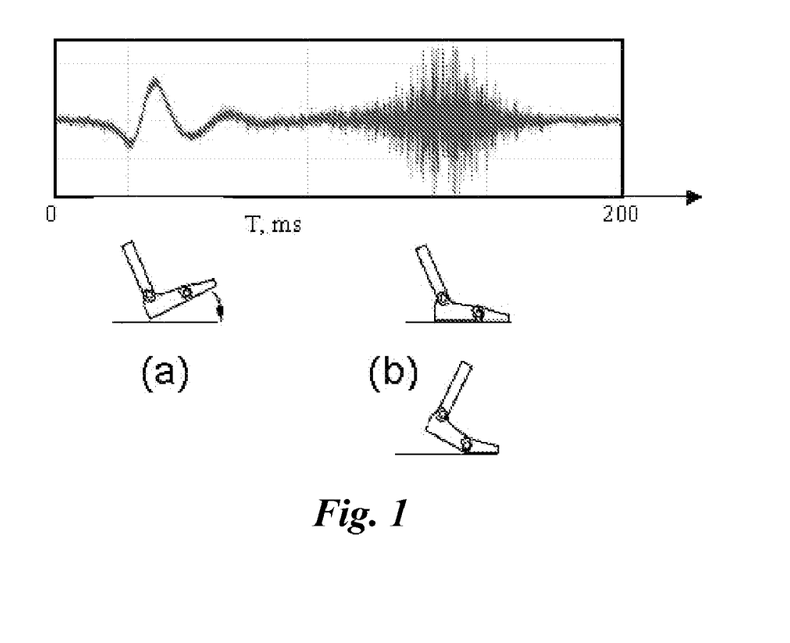
FIG. 1 shows the two phases of foot motion that provide the major contribution to the human footstep vibration signature: (a) the heel of the leading foot contacting the floor, (b) the contact of the toe of the leading foot and the pushing motion (sliding) of the trailing foot.

An example of an aspect of the present invention can be shown using an accelerometer and a digital video recorder. An experiment to simultaneously record the vibration signal and video image of human footsteps was conducted to understand the temporal and spectral vibrations of footsteps. From this analysis, the time domain vibration of a single footstep was extracted and is shown in FIG. 1 along with the idealized biomechanical foot motion model. The peak in the vibration response of the footstep is in the first half of the step, during heel contact and mid-stance as shown on this figure. The time between these two positions (a) and (b) is approximately 100-150 ms. Three styles of walking (regular, soft, and stealthy) were investigated for a person. The regular style was characterized by a straight knee when the heel contacted the floor. The soft and stealthy styles were characterized by a curved or bent knee when the foot contacted with the floor, but, for the latter, contact with the floor was by the toe of the foot only. These styles of walking produced different vibration responses of the floor in the low-frequency range.

Figure 2:
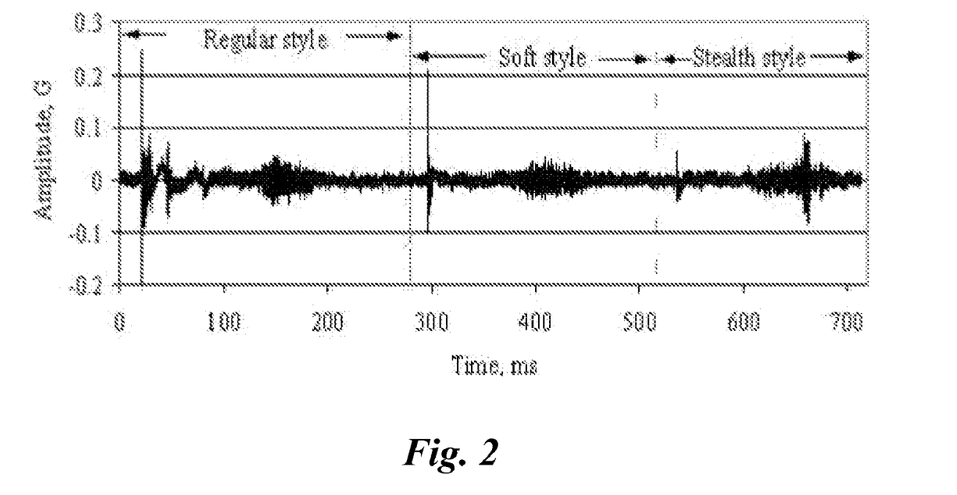
FIG. 2 shows a normal component of vibration for a single footstep for regular, soft, and stealthy styles of walking.

In FIG. 2, the normal component of vibration for a single footstep of the three walking styles is presented. While not shown here, spectral analysis showed that the frequency responses for the low-frequency range (below 200 Hz) and the high-frequency range (near the 15 kHz) had comparable magnitudes. On the other hand, the signal-to-noise ratio in the low-frequency range was less than in the high-frequency range. The difference between vibrations of the walking styles was minimal in the high-frequency range and about 15 dB in the low-frequency range. The maximum of the frequency response of the floor vibrations for the footstep in the low-frequency range was near 40 Hz for the regular walking style and near the noise floor at the same frequency for the soft and stealthy styles. An important finding is that a person can walk in a manner to substantially reduce the low-frequency energy from a footstep.

The footstep force applied to the ground/floor is due to two components: the normal force and the force tangential to the surface. The magnitude of the normal force component depends on the human motion (walking, running, etc) and the person's weight. For example, the normal force component is approximately equal to the person's weight for a typical walking style. The tangential force is governed by the horizontal motion and is equal to the force of the ground/floor reaction, or friction force. The friction force is equal to the person's weight multiplied by a coefficient of friction. Interaction of these forces with the ground or the floor in a building generates vibration.

These two components of vibration from human footsteps were observed experimentally and analyzed using Fourier transforms. The first component is generated by force normal to the surface, is well known in the literature, is concentrated in a low-frequency range below 200 Hz and, is easily reduced by the walker. The second vibration component is generated by the tangential force component, is located in a higher frequency range, and is not affected by walking style. The frequency range depends on properties of the contacting surfaces and may be extended to the ultrasonic frequencies. Below, it is shown that airborne friction sound from stealthy footstep signals can be detected at ranges greater than the traditional ground-borne low frequency footstep signal.

Without being bound by mechanism or theory, footsteps are repeatable cycles of supported surface loading by a dynamic force. This force produces the vibration response of the ground/floor in a broadband frequency range. The vibration response at the distance R from the applied force is proportional to the dynamic force and results from the product of the footstep force and the ground/floor specific transfer function. The transfer function describes the propagation of vibration between the force location and the location of the detector. The footstep force and the transfer function are the key parameters for the calculation of vibration response of ground/floor versus distance to the footsteps. The ambient noise floor limits the footstep vibration signature measurements at the distance R. This site transfer function affects the propagation of footstep vibrations.

Vibrations produced by walking or other human activities can serve as useful parameters for human detection. Early work shows the maximum value for the footstep force to be in the frequency range of 1-4 Hz. See, for example, S. Mouring, "Dynamic Response of Floor Systems to Building Occupant Activities," Ph.D. Dissertation, The Johns Hopkins University, 1992.

In the studies by Galbraith and Barton (F. W. Galbraith and M. V. Barton "Ground Loading from Footsteps," Journal of the Acoustical Society of America, 48, 5 (Part2), 1970, pp 1288-1292) and by Ebrahimpour, et al (A. Ebrahimpour, A. Hamam, R. L. Sack, W. N. Patten, "Measuring and Modeling Dynamic Loads Imposed by Moving Crowds," Journal of Structural Engineering, December 1996, pp 1468-1474), footsteps were measured on a force platform, the frequency range typically did not exceed 200 Hz.

The ground vibration responses to human footsteps with respect to distance were investigated by Cress. See D. H. Cress, "Terrain considerations and data base development for the design and testing of devices to detect intruder-induced ground motion," Vicksburg, Miss.: U.S. Waterways Experimental Station; Technical report—U.S. Army Engineer Waterways Experiment Station; M-78-1.

Cress suggested a model to predict ground vibrations from footsteps. In this model, the seismic velocity response (vibration signature) $V(\omega,R,t)$ at the distance R from human activities is a result of multiplication of the force from the footstep $F(\omega,t)$ (force signature) and a site transfer function $T(\omega,R)$ as shown in Equation 1.

$$V(\omega,R,t)=F(\omega,t)\times T(\omega,R) \quad (1)$$

In this equation, $\omega=2\pi f$, f is the frequency, R is the distance from the point at which force is applied to the ground to the point of the seismic velocity measurement, and t is time.

The site transfer function describes the propagation of vibration between two points: the location of the force (source location) and the detector location. It was experimentally shown by Cress that the transfer function is site-specific and has its maximum within the frequency range of 20-90 Hz. In this work, the spectra of vibrations V(ω) for the human activities of crawling, walking, and running were collected at four test sites. From this work the main observations were that the same human activities have different vibration spectra at different sites due to differences in the site transfer functions and, for the same site, all three activities result in very similar spectra. Concerning the vibration spectra for different sites, a shift in the maximum of the frequency response was the most prominent difference.

Figure 3:
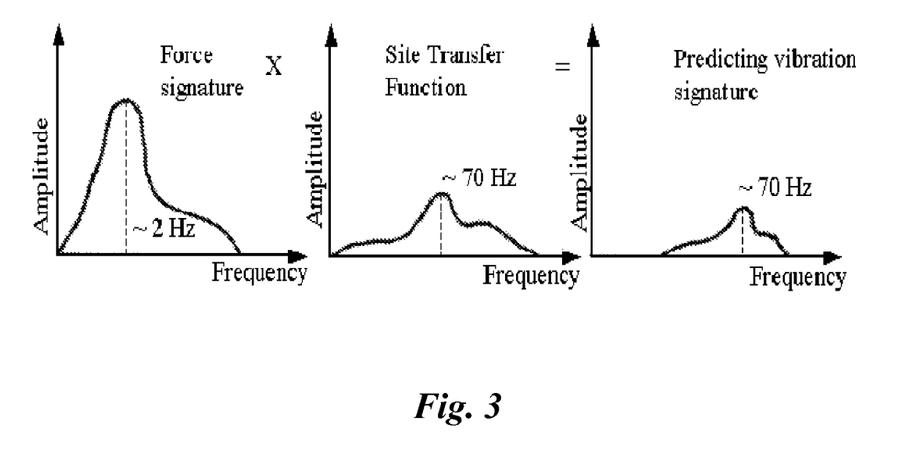
FIG. 3 shows typical Fourier spectra of human force signature, site transfer function, and vibration signature from footsteps.

The graphical illustration of Equation 1 is presented in FIG. 3, which is taken from the Cress report. The maximum in the Fourier spectrum of the force due to a footstep is in a frequency range near 2 Hz and the maximum in the spectrum of the site transfer function is near 70 Hz. Predictions of the maximum of the site vibration response are near 70 Hz.

Figure 4:
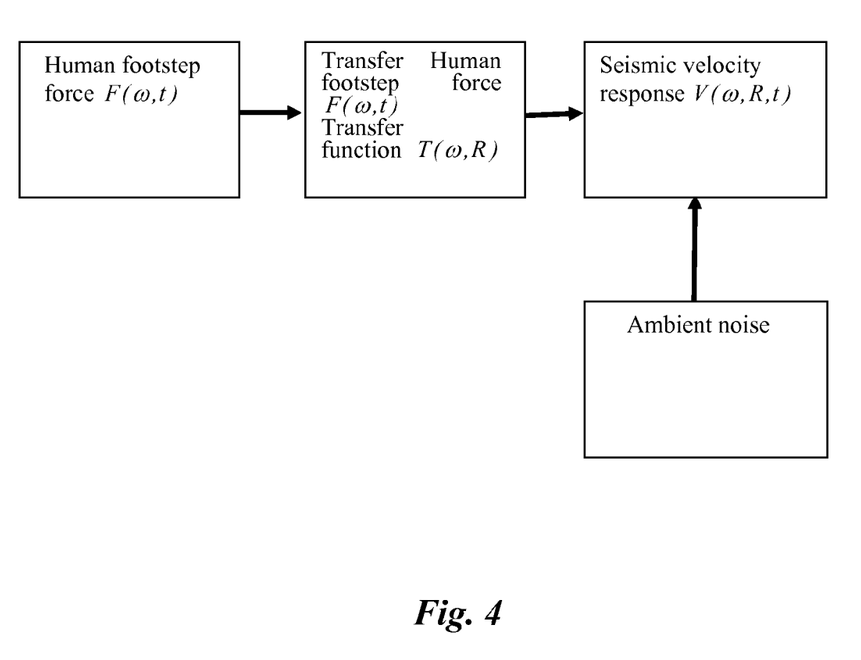
FIG. 4 shows three factors in seismic velocity response detection and recognition of a human footstep.

As shown in FIG. 4, there are three key factors in the detection of the seismic velocity response: the force of the human footstep, the transfer function of the ground or floor, and the ambient noise at the sensor location. Each of these three components has a significant influence on the possibility of seismic velocity response detection and recognition.

High-frequency bands (above 1 kHz up to ultrasonic frequencies) in the vibration and sound responses from human footsteps have been observed experimentally using broadband accelerometers and microphones in buildings. For example, see A. Ekimov, and J. M. Sabatier, "Vibration and sound signatures of human footsteps in buildings," J. Acoust. Soc. Am., 120 (2), 762-768 (2006). However, similar outdoor tests showed only the low-frequency vibration responses (below 1 kHz) of the ground to footsteps.

An aspect of the present invention is high-frequency measurements using resonant (narrow band) ceramic transducers for footstep sounds in outdoor tests. Although there may be situations where the resonant ceramic transducers are preferred, other aspects of the present invention include broadband microphones. For example, resonant ceramic transducers may have immunity to outdoor ambient noise in the low-frequency range. This high outdoor noise level decreases the dynamic range of measured signals from footsteps in the high frequencies in an audio frequency microphone. However, the resonant ultrasonic receiver naturally filters these low frequencies.

Aspects of this embodiment can be shown by tests conducted in a grassy area. The setup comprises a circular track marked on the ground with a constant distance from an accelerometer to the subject during the measurements. In these experiments, a person walked on the circular track, which was 0.2 meters wide. The median radius of the track was one meter and, depending on the length of person's stride, 9-11 steps were required to complete a full circle.

A 3-axis accelerometer was threaded into the top of a 10-centimeter spike hammered into the ground at the center of the circular track. The accelerometer was calibrated over the frequency range of 0.2 Hz-16.5 kHz and had a sensitivity of 1 V/g. A battery-powered signal conditioner amplified signals from the accelerometer. Only the component of acceleration normal to the ground surface is presented and discussed in this section. An ultrasonic (narrow band) ceramic sensor was attached to a tripod of 1.2 m height and placed 6 meters away from the center of the circular track. The ultrasonic ceramic sensor had a resonance frequency of 25.5 kHz and typical bandwidth of 1 kHz (at −6 dB). The directivity was 60° (at −6 dB). The ultrasonic ceramic sensor was calibrated at the resonance frequency of 25.5 kHz and had a sensitivity of −18 dB re 1 V/Pa. In this configuration, the beam pattern of the ultrasonic sensor covered the entire circular track. A receiving preamplifier amplified signals from the ultrasonic ceramic sensor. Data recording and processing were conducted using a two-channel, 16-bit data acquisition board and a laptop computer with SOUND TECHNOLOGY™ software.

Figure 5:
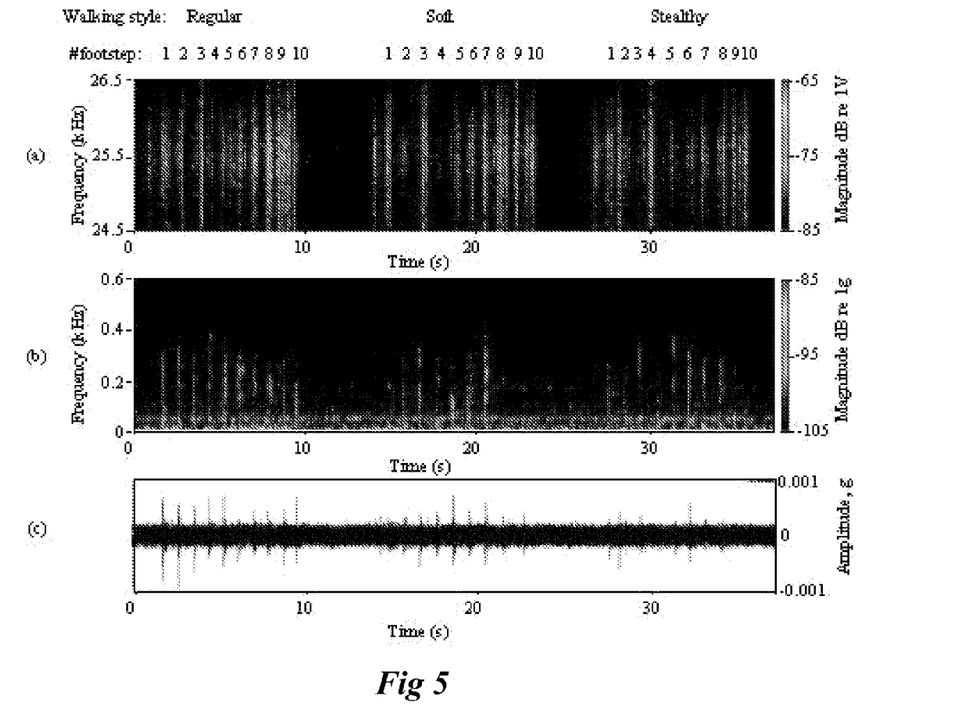

Footstep acoustic signatures for regular, soft, and stealthy walking styles of a man were measured. A man walked at a constant speed for all tested styles. A data acquisition system with a sampling rate of 64 kHz and a 32 kHz anti-aliasing filter acquired signals from the accelerometer and the ultrasonic ceramic sensor. The data (sound pressure and acceleration) for a full circle of ten footsteps for each walking style were taken and merged together in one data file and is shown in FIG. 5. Spectrograms of the sound and acceleration responses of the ground in the frequency band of 24.5 kHz-26.5 kHz for the sound and of 20 Hz-600 Hz for the acceleration are presented in FIGS. 5(a) and 5(b). The time domain signal of the acceleration is presented in FIG. 5(c).

The high-frequency vibrations above 600 Hz were not detectable by the accelerometer in this experiment; consequently, all seismic data are presented in the frequency range below 600 Hz. Qualitative comparison of the sound pressure measured by the ultrasonic ceramic sensor and vibration responses measured by the accelerometer of the walking styles shows a stable level of sound pressure signals for all walking styles in the distance range of 5-7 meters. The vibration response was less detectable for soft and stealthy styles even one meter from the detector.

Figure 6:
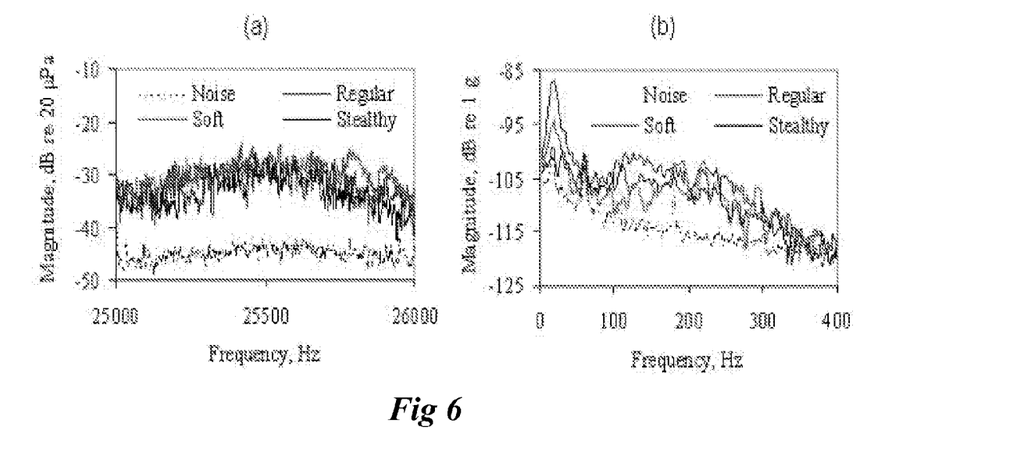
FIG. 6 shows the average Fourier spectra of ten regular, soft, and stealthy footsteps on the ground. (a) is the sound pressure at 5-7 m from a walker and (b) is the acceleration at 1 m from a walker.

In FIGS. 6(a) and (b), the average spectra of ten footsteps for each walking style are presented for sound pressure and vibration signals, respectively. The maxima of the footsteps' sound pressure responses have comparable magnitudes for all walking styles in the high-frequency range. The signal-to-noise ratio is near 15 dB. This supports the conclusions reported in A. Ekimov, and J. M. Sabatier, "Vibration and sound signatures of human footsteps in buildings," J. Acoust. Soc. Am., 120 (2), 762-768 (2006), for footstep vibration signatures for different styles of walking in buildings.

The maxima of the ground vibration response to footsteps are in the frequency band near 19 Hz for all walking styles. It is of interest to compare the magnitudes of the sound pressure at 25.5 kHz and the acceleration at 19 Hz. A comparison of the walking styles and maxima of the vibration responses shows that the vibration maxima are related to the walking styles (FIG. 6(b)). Soft and stealthy walking reduced the vibration response of the ground by 7.5 dB and 12.5 dB, respectively, relative to regular walking. As a result, the range for footstep detection is reduced. However, since the dispersion in the pressure magnitudes for the different walking styles is within a dB or so (FIG. 6(a)), the sound pressure response in the high-frequency range has only a weak dependence on walking style.

The ultrasonic signals in the air are not strongly influenced by the walking style. Even though attenuation increases with frequency, these high-frequency friction signals are a reliable indicator of human activity. However, there may be false friction signals. Accordingly, an aspect of the invention is to complement the passive measurement with ultrasonic Doppler effects due to human body motion.

There have been numerous investigations of the human body motion Doppler signature, measured by radar systems, to study the problem of human recognition among other moving objects. See, for example, J. L. Geisheimer, E. F.

Greneker, and W. S. Marshall, "A high-resolution Doppler model of human gait," SPIE, Proceedings, Vol. 4744, 8-18 (2002); P. van Dorp, and F. C. A. Groen, "Human walking estimation with radar," IEE Proc. Radar, Sonar and Navigation, V. 150, No. 5, 356-365 (2003); M. Otero, "Application of a continuous wave radar for human gait recognition," SPIE, Proceedings, Vol. 5809, 538-548 (2005); and P. Cory, H. R. Everett, and T. H. Pastore, "Radar-based intruder detection for a robotic security system," SPIE Proc. 3525: Mobile Robots XIII and Intelligent Transportation Systems, Boston, pp. 62-72 (1998); Zhaonian Zhang, Philippe O. Pouliquen, Allen Waxman, and Andreas G. Andreou, "Acoustic micro-Doppler radar for human gait imaging," J. Acoust. Soc. Am. Express Letters, 121 (3), DOI: 10.1121/1.2437842 (2007); all of which can be used in embodiments of the present invention.

In general, this aspect involves the transmission of electromagnetic waves to the human body and registration of the back-scattered waves by the radar. The reflected waves are frequency-modulated by time-varying motions of human body parts, so the time-frequency analysis (spectrograms or dynamic spectra) is widely used. The transmitted frequency typically is in the range of 2.4-100 GHz.

In more preferred embodiments of the present invention, an ultrasonic method can be applied for the study of the human motion Doppler signature. The physical principles (emitting and receiving the backscattered energy) and signal processing of ultrasonic and electromagnetic techniques are similar. The differences in the physical nature of waves (sound and electromagnetic) and in the speeds of wave propagation ($C_s$=343 m/s for the sound waves and $C_e$=300,000,000 m/s for the electromagnetic waves) make the ultrasonic measurements simpler and much less costly than electromagnetic measurements. For example, a desirable Doppler carrier wavelength in air is approximately one centimeter or so and at an acoustic frequency of 40 kHz, while the same electromagnetic wavelength is 35.0 GHz. Such high-frequency signals require much more sophisticated electronics for data acquisition and analysis. Low cost ultrasonic transducers are readily available for operation in air.

In embodiments of the present invention, a signal, such as an ultrasonic signal, is transmitted continuously into an area. If a human moves into an area, he or she reflects the ultrasonic waves from various body parts. The resulting Doppler signal is received and can be processed to identify characteristic human motion. Because walls are good reflectors of ultrasonic waves, human motion can be detected around corners of hallways in buildings as well as in the line of sight of the sensor.

Another advantage of measurement at ultrasonic frequencies is the availability of low-cost, digital data acquisition boards that have broad dynamic ranges up to 24-bits in the frequency range up to 96 kHz and have onboard digital signal processing and analysis features. The extended dynamic range increases the accuracy of the human motion Doppler signature analysis. Potentially, it allows for the separation of reflected signals in the Doppler signature from individual human body parts (torso, legs, arms, etc.) that have different cross-sections.

An ultrasonic Doppler sensor was designed using commercially-available ultrasonic ceramic sensors. These sensors had a resonance frequency of about 40 kHz, typical bandwidth of 2 kHz (at −6 dB), and directivity of 550 (at −6 dB). One of the sensors emitted an ultrasonic wave and the other acted as a receiver. A signal generator applied a continuous wave electrical signal at 40 kHz to the transmitter. Signals from the receiver were amplified with a low-noise preamplifier. Data processing and recording were conducted using the hardware and software mentioned above.

Using these sensors, human motion Doppler signatures were measured in the hallways of a modern building. For this experiment, a sensor was placed on a tripod of 1.2 m height and located at the center of the width of hallway. A person walked in a straight line 0.3 meter wide towards and away from the sensor. The length of the track was about 17 meters and the distance from the sensor to the track beginning was about 1 meter.

Figure 7:
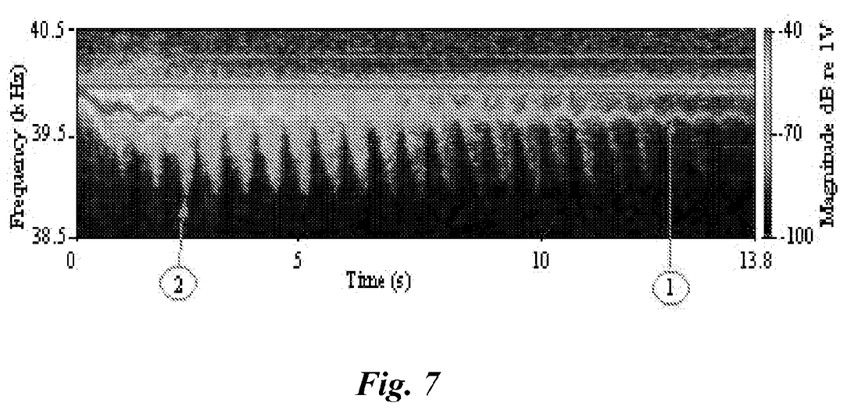
FIG. 7 shows a spectrogram of the human Doppler signature at the distance range of 1-18 meters. A person was walking away from an ultrasonic Doppler sensor (UDS).

The spectrogram of reflected waves in the frequency band of about 38.5 kHz-40.5 kHz from a person walking away from the Doppler sensor at a range of 1-18 meters is presented in FIG. 7. At the zero sec. start time, a walker was standing one meter from the sensor and then began walking with a constant speed of motion on the straight track and stopped out of sensor range. Twenty-two steps were required to complete the distance of 17 meters.

The spectrogram shows detectable values of Doppler shifts in reflected waves from a walking person at a distance of 1-18 meters on the test track. The horizontal red line (40 kHz) in the spectrogram is the sum of direct coupling between the transmitter and the receiver through the air and the reflected signal from stationary objects. The strongest amplitude reflection from a walking person corresponded to the oscillating line near the frequency of 39.7 kHz, marked by #1 in FIG. 7. Here the nominal Doppler shift was 300 Hz. The Doppler shift Δf is proportional to the object speed V $$\Delta f = \frac{2V}{C_s} f, \qquad (2)$$

where $C_s$ is the sound speed, and f is the transmitted frequency. For this case in which the frequency shift was 300 Hz (where $C_s$=343 m/s was the sound speed in air, f=40 kHz, Δf=300 Hz), the speed of the walker V follows from Equation (2):

$$V = \frac{\Delta f}{2xf} \times C_s = \frac{300}{2x40,000} \times 343 = 1.29 \text{ [m/s]}. \qquad (3)$$

The direct estimation of V from data presented on the spectrogram in FIG. 7 gives the value of:

$$V = \frac{D}{t} = \frac{17 \text{ m}}{13.8 \text{ s}} = 1.23 \text{ [m/s]}, \qquad (4)$$

D, the track length, was 17 m and t was the time needed to traverse the track by the walker 13.8 s.

The speed calculated from the Doppler shift (Eq. (3)) and from experimental geometry (Eq. (4)) is approximately the same; therefore, this strongest amplitude reflection frequency shift likely corresponds to the body part having the maximum acoustic backscatter cross section, the torso. The small oscillating frequency shifts about this frequency correspond to the torso moving back and forward over the hips as the walker moves forward.

The envelope of curves marked by #2 in FIG. 7 corresponds to the motions of the legs and arms, which have smaller cross sections than the torso, so they are less detectable with distance. However, leg and arm motions must move with greater oscillatory speeds than the torso and have larger Doppler frequency shifts in comparison with the torso motion.

A comparison of relative phases of the Doppler shifts in the curves marked #1 and envelope #2 (FIG. 7) shows that the minimum Doppler shift of the torso motion corresponds to the maximum value of leg and arm motions. The torso motion is in the opposite phase to one set of leg and arm motions and in phase to another set of leg and arm motions. The minimum value of the Doppler shift in envelope #2 ($\Delta f=0$ Hz) corresponds to the zero speed of leg and arm or the time when one leg is in contact with the floor.

Ultrasonic waves are almost completely reflected from solid surfaces, for example, from walls in buildings. They also scatter at corners. This property offers an opportunity to detect human motion by secondary reflected waves from walls (indirect method). Direct measurements of human motion involve: transmitted signal to human body—backscattered signal to receiver, while indirect measurements of human motion involve: transmitted signal to reflector to human body—backscattered signal to reflector to receiver.

Figure 8:
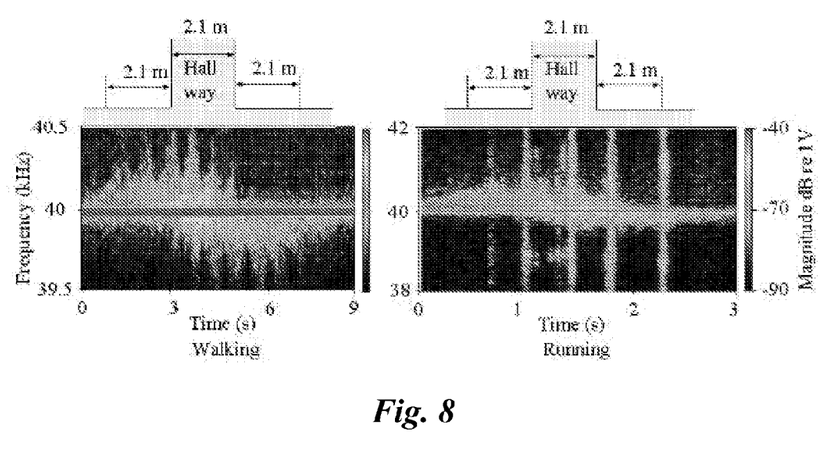
FIG. 8 is a spectrogram of the Doppler signature of a walking and running man in the orthogonal direction to the beam of ultrasonic Doppler sensor that was placed 7 m from the test track.

Direct measurements are possible with both ultrasonic and electromagnetic Doppler systems. However, indirect measurements of the human motion Doppler signature using electromagnetic radar are only possible in the case where a fully-reflected surface for electromagnetic waves exists (metal walls, for example). The indirect ultrasonic Doppler measurement of human motion, in certain conditions, allow "vision" around a corner as shown in FIG. 8.

Since the ultrasound emitted by human footsteps is occurring as a result of leg, arm and torso motion, simultaneous study of the passive and active ultrasonic methods will likely reveal new signal processing approaches to human presence detection. The Doppler sensor and ultrasonic ceramic passive receiver were set up to simultaneously record Doppler and footstep data from a walking person.

Figure 9:
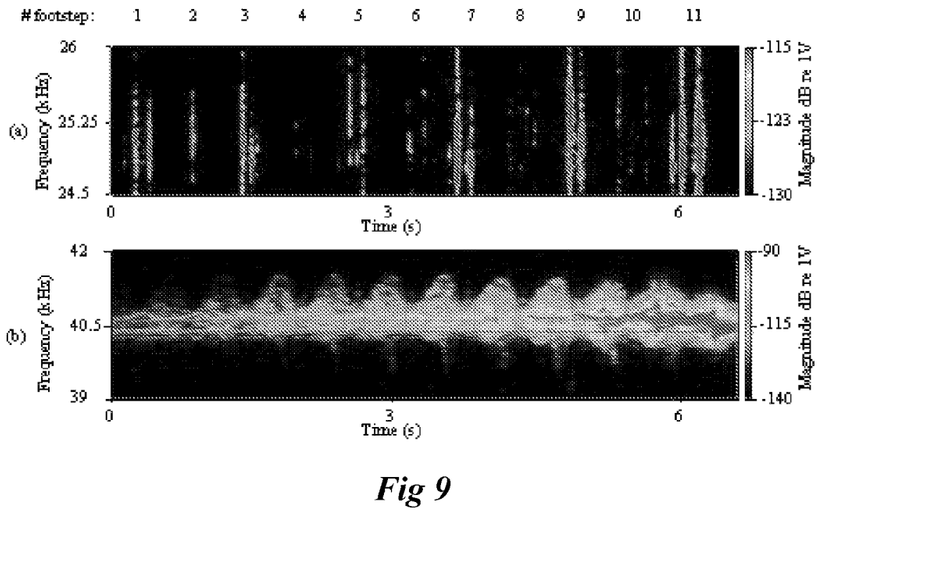
FIG. 9 is the spectrograms of (a) footstep sound pressure signature and (b) the Doppler signature of a person walking toward an ultrasonic device (UD) in the distance range of 1-9 meters.

The resulting spectrograms of the Doppler and sound pressure footstep signatures are presented in FIGS. 9(a) and (b) in the frequency range of 39 kHz-42 kHz (Doppler signature) and of 24.5 kHz-26 kHz (footstep sound pressure signature) and for a distance range of 1-9 meters from a person walking towards the sensors. A person walked with constant speed of motion on the straight track and stopped at one meter from the sensors. Eleven footsteps were required to complete the distance of eight meters.

The spectrograms in FIGS. 9(a) and (b) show detectable values of the footstep sound pressure and the Doppler signatures at all distances. The spectrogram in FIG. 9(a) shows two responses separated in time in a single footstep signature. Here one can observe 11 sets of two closely spaced vertical lines corresponding to the 11 footsteps. These two responses (phases of footstep motion) were produced by the sliding contacts (friction) between a foot and the floor in the broadband frequency range. The first phase, the heel strike response, includes the deceleration stage of the leading foot. The second phase includes the toe contact resulting from the deceleration stage of the leading foot and the weight transfer resulting from the acceleration stage of the trailing foot. The spectrogram in FIG. 9(a) shows significantly different magnitudes in footstep signatures for the left and right legs of a walker, seen as odd and even footsteps. The human eye or ear is not capable of noticing the subtle differences in this walker's footsteps, but the ultrasound is quite dramatic and may prove useful in biomedical or biomechanical fields of research.

FIG. 9(b) is the spectrogram of the Doppler motion signal of the person walking towards the sensors and collected simultaneously with the first spectrogram shown in FIG. 9(a).

The timing of the footstep friction signals in FIG. 9(a) correlates well with the maximum Doppler shift in the torso motion or the maximum speed of the back in FIG. 9(b). One expects the human back maximum speed to occur as the leading foot comes to rest and produces the maximum sound signal. Also the minimum in the torso motion will occur after this time, when the trailing leg is at maximum speed and the body is in the mid stance position. Looking at FIG. 9(b), the minimum Doppler shift in the torso motion is seen to occur between each of the footstep signals in FIG. 9(a). If one looks at the Doppler shifts due to leg motion, it is observed that the maximum in leg speed occurs at the quiet time between the footstep sound signals and this leg motion is out-of-phase with the torso motion. The simultaneous measurement of footstep sounds and Doppler frequency shift of human body motion yields data that is clearly rich in potential physical interpretation.

Figure 10:
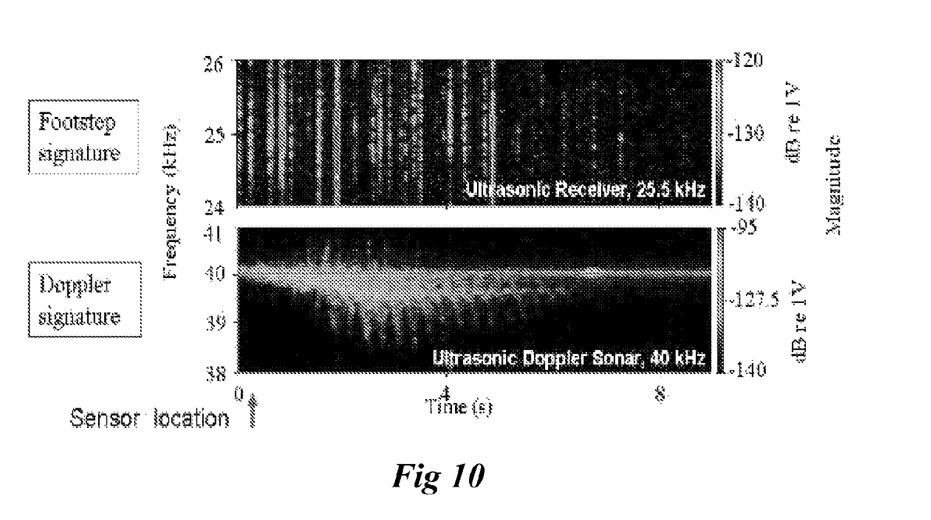
FIG. 10 shows footstep and Doppler spectrograms for a St. Bernard dog walking away from the sensor package of the UD.
Figure 11:
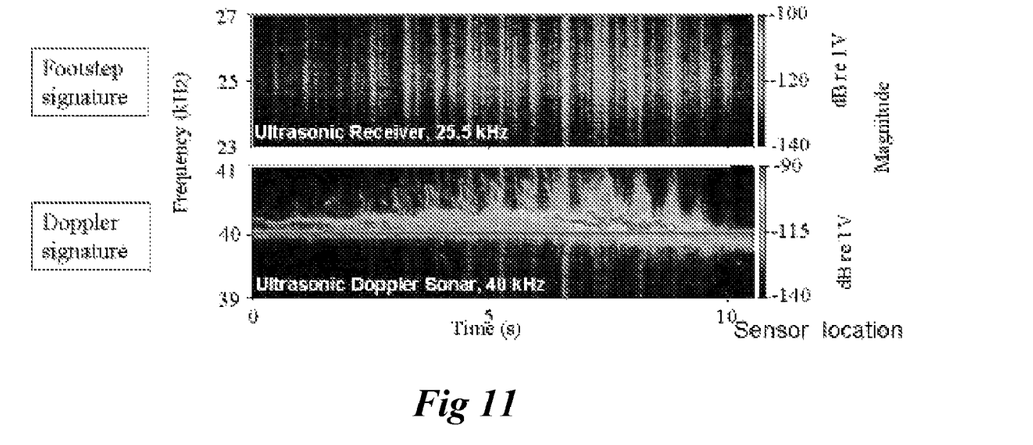
FIG. 11 shows footstep and Doppler motion spectrograms of a walking horse.

With respect to potential false alarms, initial studies were conducted to observe the footstep ultrasonic sound and Doppler signals of potential animal false alarms. Large animals can potentially create similar signals to humans. For example, border areas might have dogs, coyotes, horses, cows, rabbits, or other fauna. The present inventors have conducted initial tests to determine whether a dog or a horse could produce similar signals to a human. FIG. 10 shows the spectrograms for a St. Bernard dog while FIG. 11 shows the spectrogram for a quarter horse. As can be seen from the spectrograms, these animals do not create the characteristic double impulse of human footsteps and the Doppler signatures are significantly different, as would be expected. Key points for discrimination are the timing between footstep impulse signals and the timing between Doppler shifts associated with appendage motion.

A goal of using statistical methods in signal processing is conversion of the signal from the sensors to a final decision of YES or NO. The YES decision corresponds to the presence of a human in the area of observation and NO corresponds to the absence of a human in the observation area. Certainly, statistical methods may be applied. One of the basic, widely-used methods in signal processing for security sensors is the Markov chain [21] method. In the simplest sensor systems, the process is a simple comparison of signal levels in time sequences. Here, any event that changes the signal level corresponds to the presence of an object. If the recognition of different objects is not possible, the system will have a potentially high level of false alarms.

Taking advantage of the frequency and time characteristics of footsteps, a false alarm reduction method is illustrated. An illustration of a possible application of a Markov chain method in time-frequency analyses of footstep ultrasonic signature is presented below and in FIG. 12.

Figure 12:
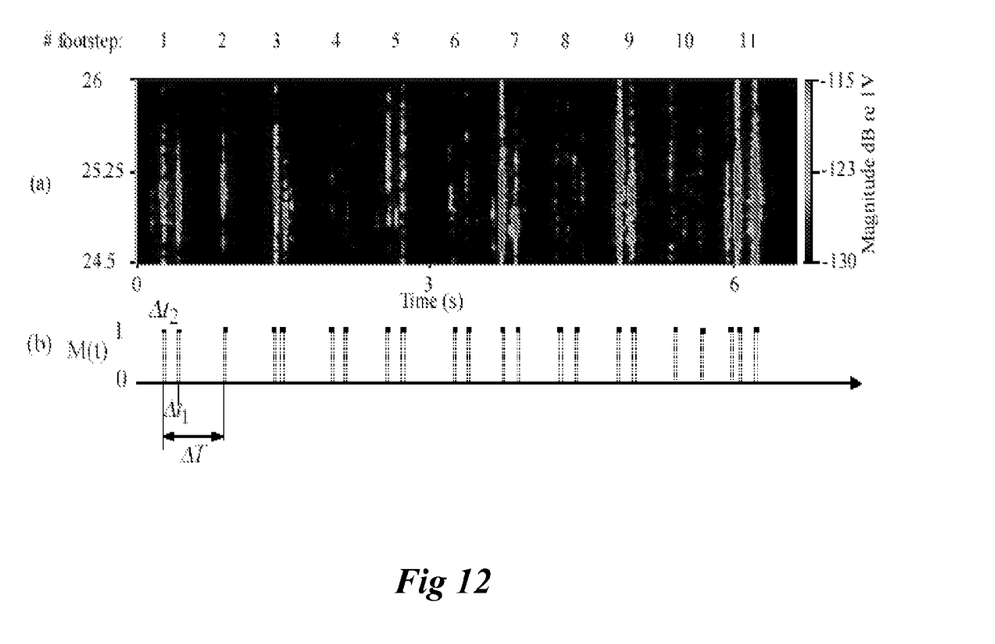
FIG. 12 shows (a) the spectrograms of footstep sound pressure signature of a person walking toward an ultrasonic sensor in the distance range of 1-9 meters, and (b) processed signal.

A Markov chain is a set of states in a time sequence, $X=\{x_1; x_2; \ldots; x_n\}$. Where, $x_i$ corresponds to an event at time i. The analog signal from a sensor is digitized by the data acquisition board with sampling rate S. The Fast Fourier Transform (FFT) length is N. In the time domain, the length of $x_i$ is equal to N/S. In the frequency domain, the frequency resolution of each spectral line $x_i$ is equal to the S/N. In the time-frequency spectrogram, xi corresponds to the FFT at a time ti, for example. $x_i$ is a vector. This is a vertical line or one FFT in FIG. 12(a) or a Markov state. X is a matrix. The FFT is integrated to obtain the state value. This transforms the X matrix into a vector.

The Markov chain process starts in $x_1$ state and moves successively from one state to another. If the chain is currently in state $x_i$, then it moves to state $x_{i+1}$ at the next time step with a probability denoted by $p_{i,i+1}$, and this probability does not depend upon prior states of the chain. Next, $x_i/x_{i+1}$ (i= 1, 2 ...) is calculated over the frequency band of the ultrasonic footstep sensor and the value $M_{i,i+1}$ is plotted as a function of time FIG. 9(b). The Markov chain values are defined as:

$$M_{i,i+1} = \begin{cases} 0, & \text{if } [x_i/x_{i+1}] = 1 \\ 1, & \text{if } [x_i/x_{i+1}] \gtrless 1 \end{cases} \quad (5)$$

A value of 0 corresponds to the noise floor or NO and 1 corresponds to an event or high level in the received ultrasound signal.

The ultrasonic signals from footsteps are very rich in signal attributes that are unique to humans and can be incorporated into the signal processing. In summary, the human physical model for the passive ultrasonic footstep signature has the following characteristics that make it appropriate for analysis: human walking is a periodic process in which the maximum frequency does not exceed 4-5 Hertz, depending upon the type of activity. Typical times for the periodic footstep rate for regular walking is approximately $\Delta T$=500 s-1000 ms; and detailed analysis of a single footstep shows that the typical duration of contact of a footfall with the surface is in the time range of $\Delta t_1$=100 ms-200 ms and the two impulses in a single footstep for regular walking have a typical time range of $\Delta t_2$=10 ms-30 ms.

In addition to the detection of the duration of footsteps as described herein, other embodiments of the present invention include further steps on the processing method to allow for extraction and recognition of human-specific time-frequency signatures and differentiates them from signals of other moving and stationary objects.

An element to this embodiments of signal processing of the present invention is the time-frequency localization of human signatures in signals produced a human motion. The algorithm of time-localization is based on the specific time duration in human footstep signatures described first by Galbraith and Barton for low-frequency seismic signals (in the range of a few Hertz) and extended then by the present inventors to include the broadband frequency vibration and sound signals (from a few Hertz up to the ultrasonic frequencies). The friction from human footsteps creates repeatable broadband frequency signal envelopes that can be passively detected by narrowband ultrasonic detector.

The algorithm of frequency-localization is based on using multiple parallel band-pass-filters (BPF) to extract a human footstep signature from the signals and then analyzing the signal envelopes for each of the filter in parallel. This processing algorithm increases the signal-to-noise ratio (SNR) and the effective range for human detection.

The algorithm of human recognition from other moving targets is based on the specific periodicity or cadence frequency analysis of human footsteps.

The present inventors have applied this signal processing methodology to two human personnel acoustic signatures: the footstep force on the ground and the oscillatory motion of human body appendages. This approach has shown SNR advantages.

In summary, this embodiment comprises the steps of (i) detection the specific time duration of footstep signals, (ii) time/frequency localization of footstep signals, and (iii) extraction the specific periodicity (cadence frequency) in footstep signals.

The methodology for step (i) is described above. The time duration of a footstep for regular walking was found to be in the range of about 100-150 ms. The aim of this step is to localize only the parts of the signal containing human signatures. This step increases the signal-to-noise ratio (SNR) in data flow from the sensor detector.

After finding the time duration of human-specific signals in step (i), this signal needs to be extracted from the sensor data flow. Step (ii) involves two components: time localization and frequency localization. For the time localization, the human-specific time duration (step (i)) is used with an overlap method. The time overlap allows detection of the footstep signal by using a sliding window equal in size to the footstep time duration and with at least about 75% of time overlap (or more up to about 99%). This increases the SNR. For the frequency localization, parallel band pass filtering (BPF) is used. The number of filters is determined by dividing the frequency range of detector used for the measurements by the filter size. The filter size is the reciprocal value of the size of sliding time window presented above (which is equal to the time duration of a footstep signal). The outputs are the root mean square (RMS) magnitudes of signal which are used for step (iii) step of this analysis.

After steps (i) and (ii), the envelopes of the signals are available for step (iii) of the analysis. To extract and track the human-specific cadence frequency, which is determined by the footstep rate (usually less than 3 Hz), a short time Fourier transform (STFT) is applied with a time window greater than the time duration of 3-4 footsteps. The largest line size in time in a spectrogram of a cadence frequency and its harmonics corresponds to the maximum SNR for the particular BPF.

The invention thus being described, it will be apparent to those skilled in the art that various modifications and variations can be made in the present invention without departing from the scope or spirit of the invention.

Other embodiments of the invention will be apparent to those skilled in the art from consideration of the specification including the claims, and practice of the invention disclosed herein.

Unless otherwise indicated, all numbers expressing quantities, specifically amounts set forth when describing experimental testing, are to be understood as being modified in all instances by the term "about." Accordingly, unless indicated to the contrary, the numerical parameters set forth in the Specification and Claims are approximations that may vary depending upon the desired properties sought to be determined by the present invention.

Throughout this disclosure, and particularly in the reference list below, various publications are referenced. All references cited herein are expressly incorporated herein by reference in their entirety and are considered to be part of this disclosure.

REFERENCES

K. M. Houston and D. P. McGaffigan, "Spectrum Analysis Techniques for Personnel Detection Using Seismic Sensors," SPIE, Proceedings on Unattended Ground Sensor Technologies and Applications, Vol. 5090, 162-173 (2003).

Ekimov, and J. M. Sabatier, "Vibration and sound signatures of human footsteps in buildings," J. Acoust. Soc. Am., 120 (2), 762-768 (2006).

H. E. Bass and L. N Bolen, "Ultrasonic background noise in industrial environments," J. Acoust. Soc. Am. 78 (6), 2013-2016 (1985).

Ekimov, and J. M. Sabatier, "Broad frequency acoustic response of ground/floor to human footsteps," Proceedings SPIE, Vol. 6241, OL-1-8 (2006).

J. L. Geisheimer, E. F. Greneker, and W. S. Marshall, "A high-resolution Doppler model of human gait," SPIE, Proceedings, Vol. 4744, 8-18 (2002).

P. van Dorp, and F. C. A. Groen, "Human walking estimation with radar," IEE Proc. Radar, Sonar and Navigation, V. 150, No. 5, 356-365 (2003).

M. Otero, "Application of a continuous wave radar for human gait recognition," SPIE, Proceedings, Vol. 5809, 538-548 (2005).

P. Cory, H. R. Everett, and T. H. Pastore, "Radar-based intruder detection for a robotic security system," SPIE Proc. 3525: Mobile Robots XIII and Intelligent Transportation Systems, Boston, pp. 62-72 (1998).

E. Ekimov and J. M. Sabatier, "Passive and active ultrasonic methods for human motion detection," Proc. Military Sensing Symposium on Battlefield Acoustics and Magnetic Sensors (2006).

V. Magori, "Ultrasonic sensors in air," IEEE Ultrasonic symposium, Proceedings, pp. 471-481 (1994).

Zhaonian Zhang, Philippe O. Pouliquen, Allen Waxman, and Andreas G. Andreou, "Acoustic micro-Doppler radar for human gait imaging," J. Acoust. Soc. Am. Express Letters, 121 (3), DOI: 10.1121/1.2437842 (2007).

Monika Kohle and Dieter Merkl, "Analyzing Human Gait Patterns for Malfunction Detection", Proceedings of the 2000 ACM symposium on Applied computing, Como, Italy, 2000, Volume 1, pp 41-45.

F. W. Galbraith and M. V. Barton "Ground Loading from Footsteps," Journal of the Acoustical Society of America, 48, 5 (Part2), 1970, pp 1288-1292

Ebrahimpour, A. Hamam, R. L. Sack, W. N. Patten, "Measuring and Modeling Dynamic Loads Imposed by Moving Crowds," Journal of Structural Engineering, December 1996, pp 1468-1474.

S. Mouring, "Dynamic Response of Floor Systems to Building Occupant Activities," Ph.D. Dissertation, The Johns Hopkins University, 1992.

D. H. Cress, "Terrain considerations and data base development for the design and testing of devices to detect intruder-induced ground motion," Vicksburg, Miss.: U.S. Waterways Experimental Station; Technical report—U.S. Army Engineer Waterways Experiment Station; M-78-1.

L. L. Beranek, "Acoustical measurements," AIP, Woodbury, N.Y., (1988).

R. J. Urick, *Principles of underwater sound*, Peninsula Publishing, Los Altos, Calif., (1983).

A. A. Markov. "Extension of the limit theorems of probability theory to a sum of variables connected in a chain", reprinted in Appendix B of: R. Howard. *Dynamic Probabilistic Systems, Volume* 1: *Markov Chains*. John Wiley and Sons, 1971.

D. E. Kleinert, D. G. Wren, C. Smith, and J. P. Chambers, "Development of an acoustic system to monitor suspended sediments in fluvial systems," Proc. 8th Federal Interagency Sedimentation Conference, Reno, Nev. Apr. 4, 2006.

We claim:

1. A method of detecting a human, comprising:
    (a) measuring the ultrasonic signal emitted from human footsteps;
    (b) measuring the human body motion Doppler signature;
    (c) reviewing the measurements of steps (a) and (b); and
    (d) determining the presence of a human.

2. The method of claim 1, wherein steps (a) and (b) are performed simultaneously.

3. The method of claim 1, wherein the determination step (d) indicates the presence of a human in an enclosure.

4. The method of claim 1, wherein the determination step (d) indicates the presence of a human in an outdoor area.

5. The method of claim 1, wherein the measurement step (a) comprises the utilization of microphone sensors for human footstep detection.

6. The method of claim 5, wherein the microphone sensors comprise ultrasonic microphone sensors.

7. The method of claim 6, wherein the ultrasonic microphones measure frequencies in a narrow band frequency range.

8. The method of claim 7, wherein the ultrasonic microphones measure frequencies in the range of about 24-26 kHz.

9. The method of claim 6, wherein the ultrasonic microphones measure frequencies in the range of about 24-26 kHz.

10. The method of claim 7, wherein the ultrasonic microphones measure at least one of the toe slap or weight transfer portions of the human footstep signature.

11. The method of claim 1, wherein the review step (c) includes the measurement of the sound pressure signature from human footstep signals.

12. The method of claim 11, wherein the review step (c) comprises a Fourier spectrum mathematical operation of the sound pressure signal.

13. The method of claim 12, wherein the Fourier spectrum is considered as a function of time and a time/frequency analysis is conducted.

14. The method of claim 1, wherein the measure step (b) comprises transmitting waves to a human body, and receiving the reflected or back-scattered waves.

15. The method of claim 14, wherein the reflected waves are frequency-modulated by time-varying motions of human body parts.

16. The method of claim 1, wherein the measurement step (b) comprises a transmitter to emit a carrier signal and a receiver to recognize a human motion modulated carrier signal.

17. The method of claim 14, wherein the transmitting waves are ultrasonic waves.

18. The method of claim 14, wherein the transmitting waves are chosen from sound and electromagnetic, radar, ultrasound, laser, IR, or terahertz waves.

19. The method of claim 14, wherein Doppler signature is measured by transmitting and receiving ultrasonic waves of a resonance frequency of about 20 kHz to about 10 kHz.

20. The method of claim 19, wherein the frequency of transmitting ultrasonic waves is about 40 kHz.

21. The method of claim 16, wherein the human motion modulated carrier signal comprises a recognition of a frequency shift of human body motion when the arms and legs move characteristically in relation to the torso.

22. The method of claim 1, wherein step (a) comprises measuring the timing between the footstep signal, and step (b) comprises measuring Doppler shifts associated with appendage motion, and step (c) comprises a comparison of the two to determine the presence of a human.

23. The method of claim 1, wherein steps (c) and (d) comprise utilization of the time-frequency analysis to review data obtained in steps (a) and (b) and compare that data to a standard value.

24. The method of claim 23, wherein the Markov chain method is used for time-frequency analysis.

25. The method of claim 1, wherein the method is applied to walking or running vertebrate animals.

26. The method of claim 1, further comprising the steps of (1) time frequency localization of footstep signals and (2) extraction of the specific periodicity in footstep signals.

27. The method of claim 26, wherein (1) includes parallel band pass filtering.

28. The method of claim 26, wherein (2) includes the application of a short time Fourier transform (STFT).

* * * * *